(12) United States Patent
Kalidindi

(10) Patent No.: US 6,339,966 B1
(45) Date of Patent: Jan. 22, 2002

(54) BULK POWDER SAMPLER WITH REMOVABLE PARTITIONS AND METHOD OF USING

(76) Inventor: Sanyasi R. Kalidindi, 15 Edinburg La., East Brunswick, NJ (US) 08816-5242

(*) Notice: Subject to any disclaimer, the term of this patent is extended or adjusted under 35 U.S.C. 154(b) by 0 days.

(21) Appl. No.: 09/679,047

(22) Filed: Oct. 4, 2000

(51) Int. Cl.⁷ ................................................ G01N 1/00
(52) U.S. Cl. .................................. 73/864.31; 73/864.64
(58) Field of Search ........................ 73/863.33, 863.31, 73/864.63, 864.64, 864.65, 864.66, 864.67, 864.31

(56) References Cited

U.S. PATENT DOCUMENTS

| | | | |
|---|---|---|---|
| 230,121 A | * 7/1880 | Frost ........................ | 73/864.64 |
| 1,078,847 A | * 11/1913 | Grauenfels ................ | 73/864.64 |
| 1,256,413 A | * 2/1918 | Wiswell .................... | 73/864.64 |
| 2,185,651 A | 1/1940 | Sollie | |
| 2,694,931 A | 11/1954 | Handley | |
| 2,875,615 A | 3/1959 | Ulvin | |
| 2,968,184 A | 1/1961 | Archer | |
| 3,065,637 A | 11/1962 | Landes | |
| 3,080,760 A | 3/1963 | Piersma | |
| 3,091,968 A | * 6/1963 | Platzer .................... | 73/864.64 |
| 3,207,321 A | * 9/1965 | Joyce ...................... | 211/126.5 |
| 4,088,025 A | * 5/1978 | Foster et al. ............. | 73/863.33 |
| 4,283,946 A | * 8/1981 | Bowser et al. ........... | 73/864.31 |
| 4,442,721 A | 4/1984 | Singer | |
| 4,660,423 A | 4/1987 | Armstrong et al. | |
| 4,744,256 A | 5/1988 | Niskin | |
| 4,790,198 A | 12/1988 | Awtry et al. | |
| 4,911,026 A | * 3/1990 | Keives .................... | 73/864.64 |
| 5,337,620 A | 8/1994 | Kalidindi | |
| 5,440,941 A | 8/1995 | Kalidindi | |
| 5,616,867 A | * 4/1997 | Fox et al. ................ | 73/861.62 |

FOREIGN PATENT DOCUMENTS

| | | |
|---|---|---|
| DE | 285639 | 12/1990 |
| SU | 204682 | 10/1967 |

* cited by examiner

Primary Examiner—Hezron Williams
Assistant Examiner—Charles D. Garber
(74) Attorney, Agent, or Firm—Richard C. Litman

(57) ABSTRACT

A bulk sampling device for sampling mixtures of powder and semi-solid compositions. The sampling device comprises an apertured hollow outer tubular casing for receiving an inner receiving rod with adjacent non-communicating sample ports for holding sampled materials. The inner rod also contains removable partitions located between each sample port thereby forming non-communicating sample ports and diminishing the risk of leakage and contamination between each port. The removable partitions, located between the sample ports, are dimensioned and positioned within the partition receiving slots such that each partition remains trapped between the outer hollow tubular casing and the receiving rod when the device is assembled. The distal end of the device has a solid cone, and the proximate end has a handle to manipulate and rotate the inner receiving rod and sample ports to obtain volumetric sampling.

9 Claims, 6 Drawing Sheets

BULK POWDER SAMPLER WITH REMOVABLE PARTITIONS AND METHOD OF USING

BACKGROUND OF THE INVENTION

1. Field of the Invention

The present invention relates to bulk sampling devices, and more particularly, to improved bulk sampling devices having removable partitions to form non-communicating adjacent sample ports, and their method of use.

2. Description of the Related Art

In the manufacture of pharmaceutical dosage forms, one of the critical processing steps is the blending of the active ingredient(s) with the inactive ingredient(s) in a blender or mixer. This step becomes even more critical in case of solid dosage forms, such as tablets and capsules, because the dry powders of the active ingredient(s) and the inactive ingredient(s) tend to segregate or separate after blending resulting in non-uniform distribution of the active ingredient (s) in the finished product. Therefore, before further processing of such blends, bulk samples are taken from different places in these blends and analyzed to check whether or not the active ingredient(s) is uniformly distributed or not. Such a test is known in the trade as a content uniformity test or a homogeneity test, and requires unit-dose samples with sample size equal to about one dose of the product. My prior U.S. Pat. Nos. 5,337,620, and 5,440,941 describe sampling devices used for unit-dose sampling. In addition to unit-dose sampling, bulk samples are also needed in order to perform physical tests, such as particle size distribution, bulk density, moisture content, etc.

Several types of bulk sampling devices are available in the market for the purpose of bulk sampling. Some of these devices are comprised of a single tube with a long cavity on it. Some others have a tube within a tube with multiple sample ports on the tubes with or without partitions. However, the partitions on these samplers are permanently welded in place, and it is very difficult to clean behind these partitions. In addition, these samplers with permanent partitions do not offer the possibility of using the sampler without the partitions, if desired.

The present invention overcomes the problems associated with the currently available bulk samplers by providing a bulk sampling device which has removable partitions, thus making it possible to clean the sampler to good manufacturing practice standards, and also offering the flexibility of using the sampler with or without the partitions in order to obtain discrete samples from different locations or one composite core sample.

A number of patents have been issued that address numerous sampling devices and techniques of various materials will be discussed herein.

U.S. Pat. No. 5,337,620 issued to Kalidindi on Aug. 16, 1994 teaches a multiple sampling device and method of using the same, having removable sampling dies located within a receiving a rod placed in a tubular casing. U.S. Pat. No. 5,440,941 issued to Kalidindi on Aug. 15, 1995 teaches an extendable multi-segmented sampling device and method of using the same, containing sampling dies having cavities of varying volumes located within an extendable, segmented receiving rod that is placed in an extendable, segmented tubular casing.

Italian Patent No. 484,331 issued on Nov., 1954 to Dino consists of an inner tube containing partitioned volume with apertures for each compartment, an outermost tube, and an intermediate tube with apertures which align with both the inner tube's apertures and corresponding apertures in the outermost tube. A portion of the second tube's apertures contains a filter. The innermost tube and the intermediate tube have separate handles for alignment of their respective apertures with the apertures of the outer tube in order to take samples of an immiscible liquid system. There is no disclosure of a bulk sampling device having removable partitions between non-communicating sample ports or a handle having multi-setting positions, a separate cone tip, or operation of his sampler without the essential intermediate tube and associated filters.

In U.S. Pat. No. 4,790,198 issued on Dec. 13, 1988 to Jon Awtry et al. teaches a grain probe having an inner tubular member's openings aligned with the outer tubular member's opening to take grain samples. The grain probe has a pointed end to aid in the penetration of the grain pile. There is no disclosure of a bulk sampling device having removable partitions between non-communicating sample ports or a handle having multi-setting positions, or the removability of the pointed end.

U.S. Pat. No. 3,080,760 issued on Mar. 12, 1963 to Henry D. Piersma teaches a disposable sample probe for bulk chemicals including powder. The probe is a simple two-tube device with alignment of separate cavities with the outer tube's apertures for taking samples. Again, there is no suggestion of a bulk sampling device having removable partitions between non-communicating sample ports or a handle having multi-setting positions.

U.S. Pat. No. 2,694,931 issued on May 9, 1952 to R. G. Handley teaches a sectional deep bin grain sampling and measuring probe comprising a string of separable straight cylindrical sections, united by a flexible chain, and that form internal sample grain receiving chambers.

U.S. Pat. No. 3,065,637 issued on Dec. 7, 1959 to J. T. Landes teaches sectional grain test sampling and measuring probe for removing grain samples at different levels. The sampling probe comprises a point section, a handle section and an intermediate section adapted to be separably connected, and dissembled, such as for cleaning purposes.

U.S. Pat. No. 2,875,615 issued on Mar. 3, 1959 to Orrion A. Ulvin teaches a grain and seed probe sampling device which utilizes a spiral element within an apertured outer tube. However, the sampling device disclosed in Ulvin does not have removable partitions between non-communicating sample ports.

U.S. Pat. No. 4,744,256 issued on May 17, 1988 to Shale J. Niskin teaches water sampler device dropped from an airplane to obtain a single sample by utilizing a valving arrangement to open and close the sampler.

U.S. Pat. No. 2,185,651 issued on Jan. 2, 1940 to John Soiethere teaches a milk sampler including a rod with attached handle to reduce sample volume, capacity.

U.S. Pat. No. 4,660,423 issued on Apr. 28, 1987 to John M. Armstrong et al., teaches a water sampling apparatus wherein sampling is initiated by in situ puncturing of a sealed tube to obtain one sample.

German patent document DD 285,639 A5 published on Dec. 19, 1990 to Rolf Hoffman et al. teaches a sampling device where the chamber is rotatable to receive and discharge a sample.

USSR patent 204,682 issued on Jul. 28, 1967 to G. K. Kushchanov there discloses a sampler consisting of a pipe having inclined shelves. The pipe is disposed within a cylindrical body having ports and gates to allow samples to be collected as the device is axially rotated.

U.S. Pat. No. 2,968,184 issued on Jan. 17, 1961 to James R. Archer et al. teaches a sampling tube having a receiving member and a cover member. The cover member is slidable relative to the receiving member which is in the form of a tube and has holes cut therein. The device can be inserted into a material to be sampled and the cover is slid back to allow the material to enter the holes in the receiving member. The cover is then slid back into a closed position and the device is withdrawn.

Finally, U.S. Pat. No. 4,442,721 issued on Apr. 17, 1984 to Laura G. Singer discloses a soil moisture and consistency sampler comprising an elongate member with an insertable end, a handle end, and a plurality of generally transverse collecting means disposed proximate the insertable end that define soil collecting pockets.

None of the above inventions and patents, taken either singularly or in combination, is seen to describe the instant invention as claimed. Thus a bulk sampling device having removable partitions between non-communicating sample ports and method of using and cleaning the same, as well as solving the aforementioned problems are desired.

SUMMARY OF THE INVENTION

Accordingly, it is a principal object of the invention to provide a bulk sampling device or tool, and a method for utilizing the same, for obtaining bulk volumetric samples from different levels in a blender or mixer containing pharmaceutical, food, cosmetic, or the like, powders, ointments, creams or other semi-solid emulsions in one sampling attempt. The bulk sampling device comprises a removable bulk sampling inner receiving rod contained within an outer hollow apertured tubular casing.

The inner receiving rod contains a handle, a guide pin, an inner wall, an outer wall and non-communicating bulk sample ports or cavities. The bulk sample ports are separated by a plurality of removable partitions located between each adjacent sample port. Each removable partition is seated within a partition receiving slot located adjacent each bulk sample port such that each partition is retained therein when the receiving rod is completely inserted in the outer tubular casing.

The outer hollow tubular casing contains a grooved guide pin receiving pattern and a row of apertures. The apertures are slightly smaller than the exposed area size of the bulk sample ports and are aligned with the location of the bulk sample ports to permit retrieval and/or discharge of a sample contained within the sample ports upon rotational movement of the inner receiving rod.

The retrieval and/or discharge of a sample is achieved by placing the inner receiving rod with non-communicating bulk sample ports completely within the hollow apertured outer tube such that the sample ports are in a closed position by misaligning the apertures and ports, and inserting the assembled sampling device into a powder blender or similar apparatus containing a sampling material. The non-communicating bulk sample ports are aligned relative to the apertures on the outer casing by manipulating and rotating the inner receiving rod, with the handle, into an open position such that sample material enters the sample ports through the apertures of the outer tubular casing, and into the bulk sample ports. After the bulk sample ports are filled, the bulk sample ports are manipulated into the closed position by offsetting the alignment between the bulk sample ports on the inner receiving rod and the apertures on the outer tubular casing, and the sampling device is removed from the sampling material. After the sampling device is removed from the sampling material, the bulk sample ports are manipulated once again into the opened position, only this time to discharge or release the sample material contained within each bulk sample port, at the desired endpoint. The partitions located within the partition receiving slots are trapped by the outer tubular casing and are thereby retained within the inner receiving rod.

It is an object of the invention to provide a bulk sampling device or tool having removable partitions between adjacent communicating sample ports in order to render the communicating ports non-communicating, to prevent contamination and leakage between neighboring ports, wherein the partitions are held snugly and securely in partition receiving slots located on the inner receiving rod.

Another object of the invention is to provide a bulk sampling device or tool having a grooved guide pin receiving pattern located on the outer tubular casing for receiving a guide pin located on the inner receiving rod to assist in the manipulation of the opening and closing of the bulk sample receiving ports.

Yet another object of the invention is to provide a bulk sampling device constructed from stainless steel, plastic or a combination of both.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
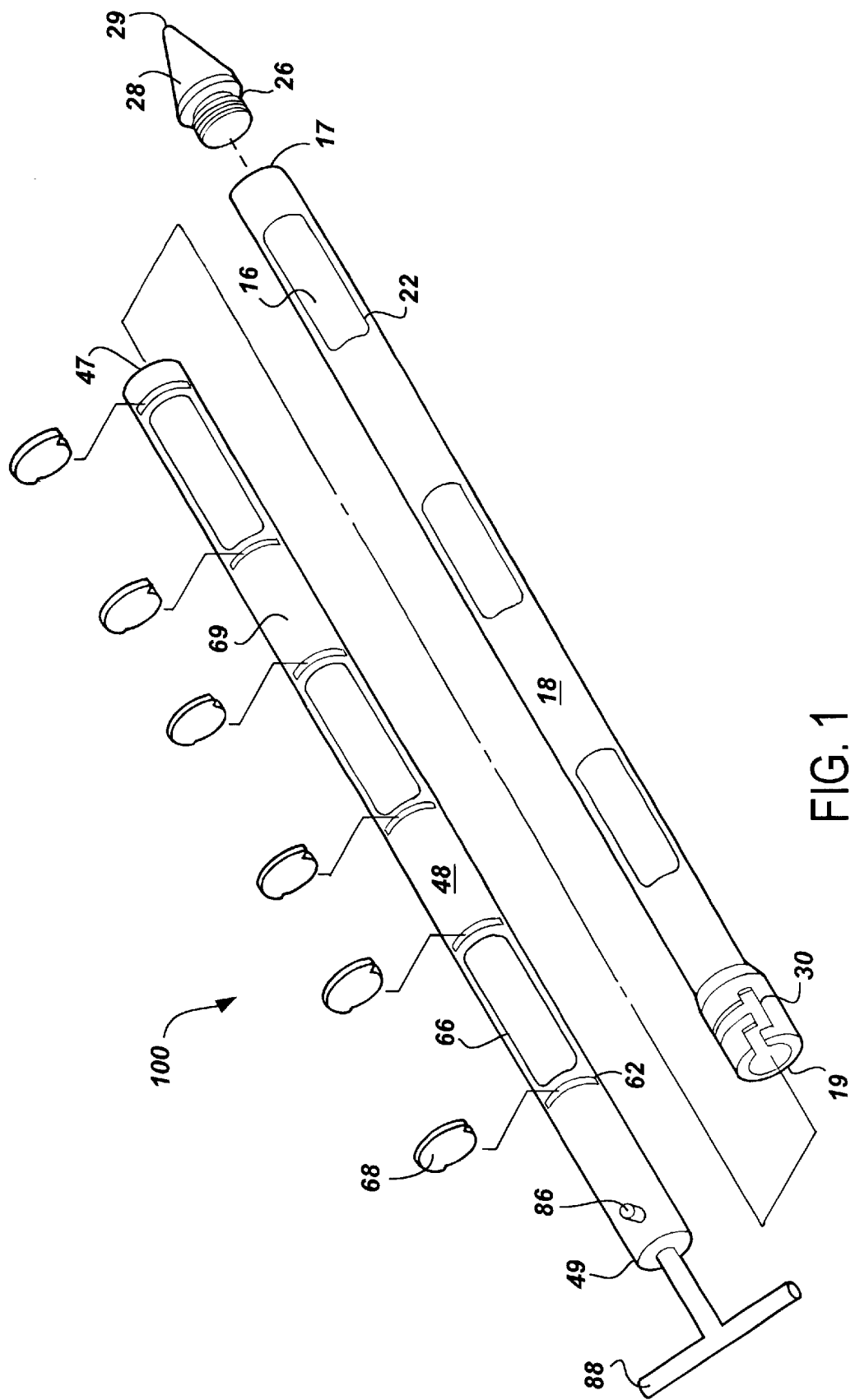
FIG. 1 is an exploded perspective view of a preferred embodiment of a bulk sampling tool according to the present invention.

FIGS. 1–6 depict the preferred embodiment of a bulk sampling device or tool 100, used for taking multiple volumetric samples from the same area and at different depths of powder or semi-solid mixtures. As seen in FIG. 1, the bulk sampling device 100 comprises a cylindrical hollow outer apertured tubular casing 18 for receiving a cylindrical removable, rotatable inner bulk sampling receiving rod 48. The hollow outer casing 18 has a predetermined length, a smooth interior wall 16 dimensioned to smoothly receive said inner receiving rod 48, a row of apertures or openings 22 (three are shown in FIG. 1 and only one is shown in FIGS. 2–6), a distal end having first engaging means 17 and an opened proximate end 19 for receiving the inner rod 48 for placement within the outer casing 18. The proximate end 19 of the outer casing 18 also contains a grooved guide pin receiving pattern 30.

The bulk sampling device 100 also contains a removable cone 28, preferably solid, having a distal end tip 29 and a proximate end having a second engaging means 26 for engaging the first engaging means end 17 of the outer casing 18, thereby closing the distal end of the outer tubular casing 18. Preferably, the second engaging means is external threading and the first engaging means is internal threading for receiving the external threading on the cone 28.

Figure 4:
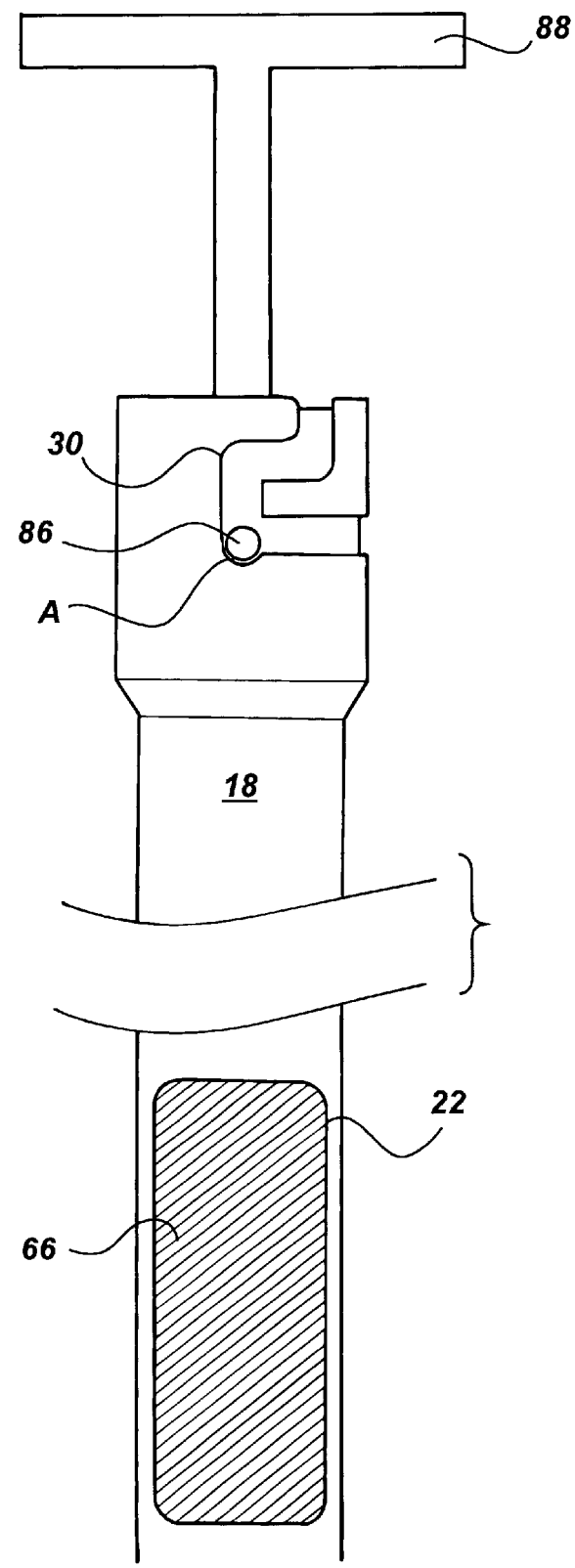
FIG. 4 is a top plan view, partially broken away, of the bulk sampling device according to the present invention, wherein a sample port is in an open position.
Figure 5:
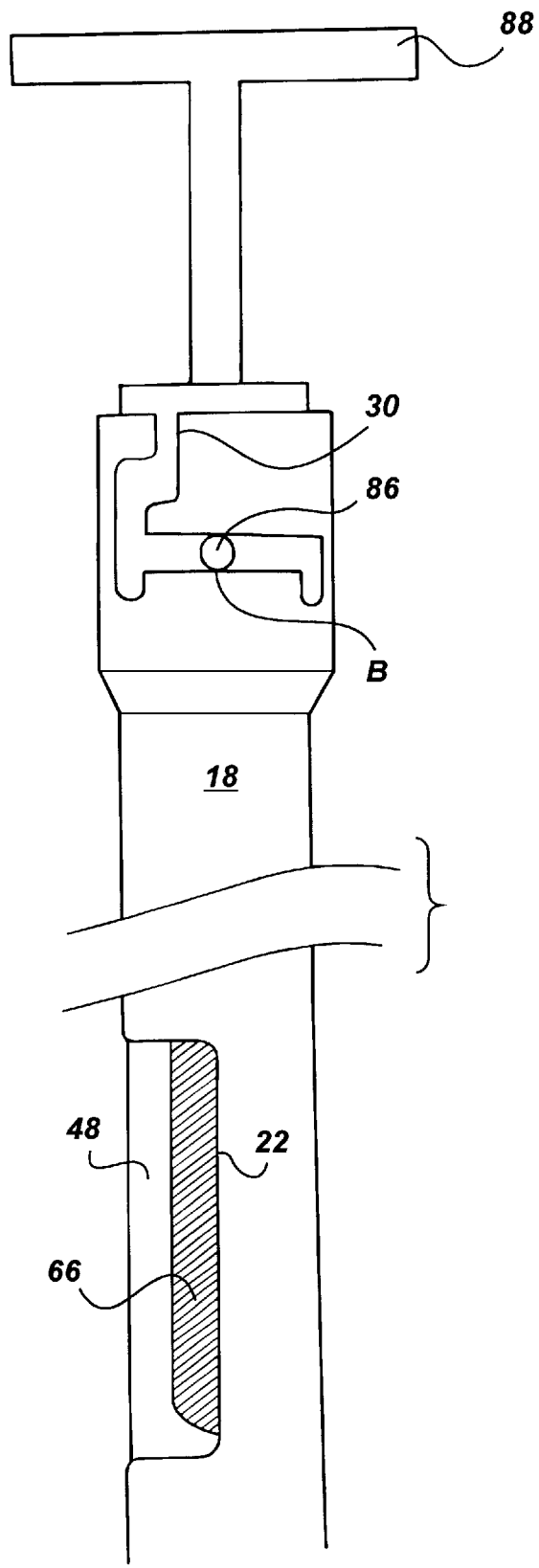
FIG. 5 is a side elevational view, partially broken away, of the FIG. 4 bulk sampling device from a vantage point approximately 45 degrees offset from the view of FIG. 4, wherein the sample port is in a partially opened position.
Figure 6:
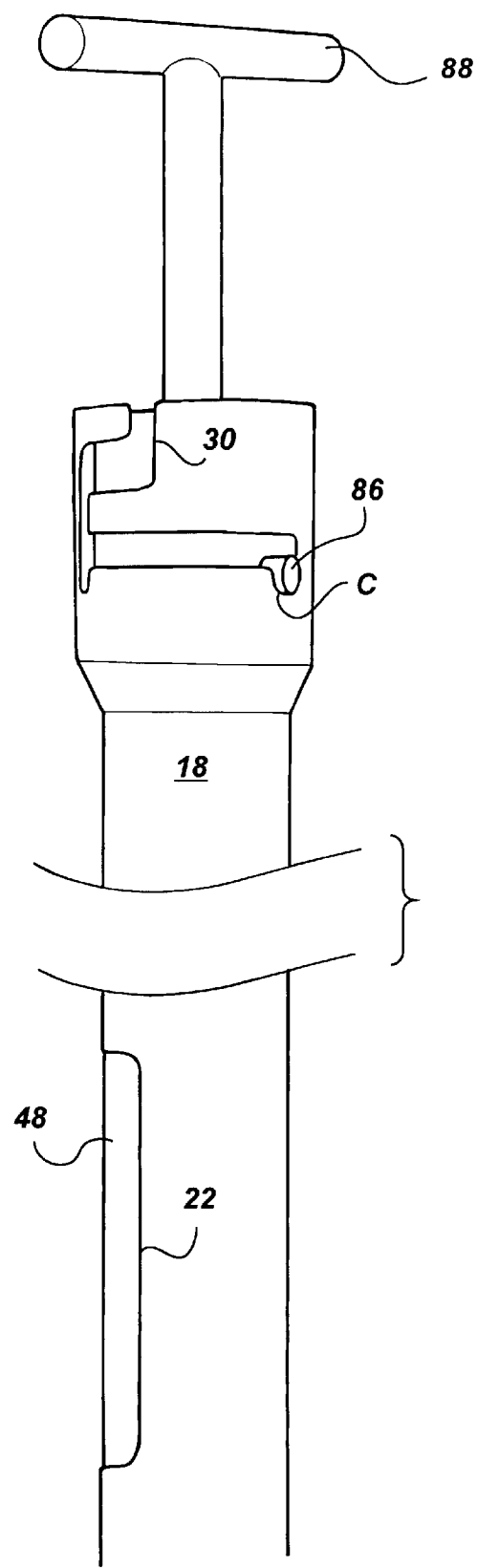
FIG. 6 is a side elevational view, partially broken away, of the FIG. 4 sampling device, viewed from a vantage point approximately 90 degrees offset from the view of FIG. 4, wherein the sample port is in a closed position.

The inner receiving rod 48 has a predetermined length for fitting snugly and removably inside the tubular casing 18, a proximate end 49, an opened distal end 47, an inner wall surface 60, an outer wall surface 69, a row of non-communicating bulk sample receiving ports 66 (three are shown in FIG. 1, and only one is shown in FIGS. 2–6), a plurality of removable partitions 68 and a plurality of partition receiving slots 62. The proximate end 49 of the inner receiving rod 48 has a handle 88 and a guide pin 86. The removable partitions 68, when positioned in the receiving slots 62, form adjacent non-communicating sample ports with the inner rod 48. The partitions 68 remain trapped within the receiving slots 62, and will not fall out of the device even when the sample ports are in an opened position, as depicted in FIGS. 4–6.

Figure 2:
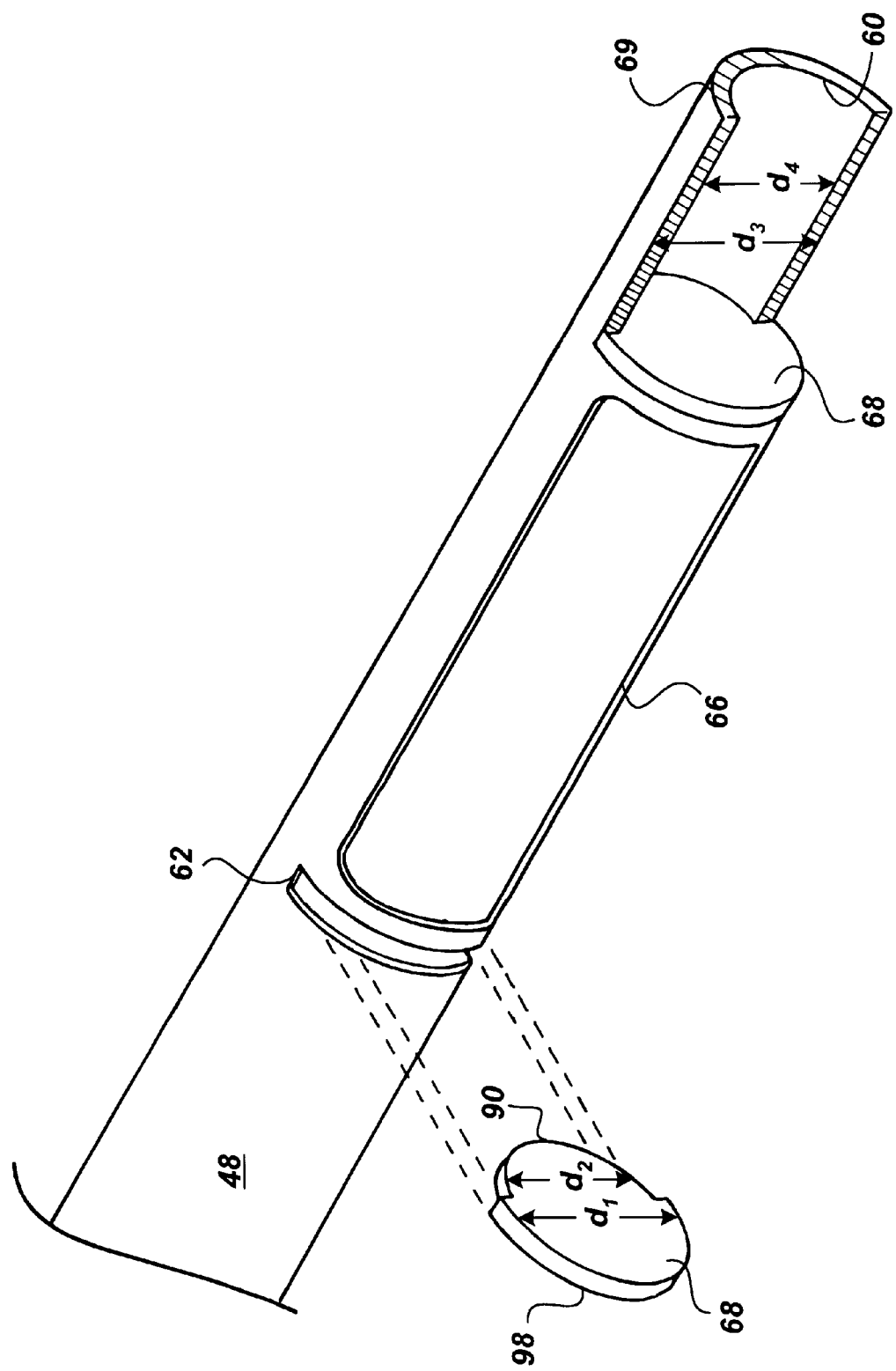
FIG. 2 is a partial cutaway exploded view of an inner receiving rod with bulk sample ports and removable partitions of the bulk sampling tool according to the present invention.
Figure 3:
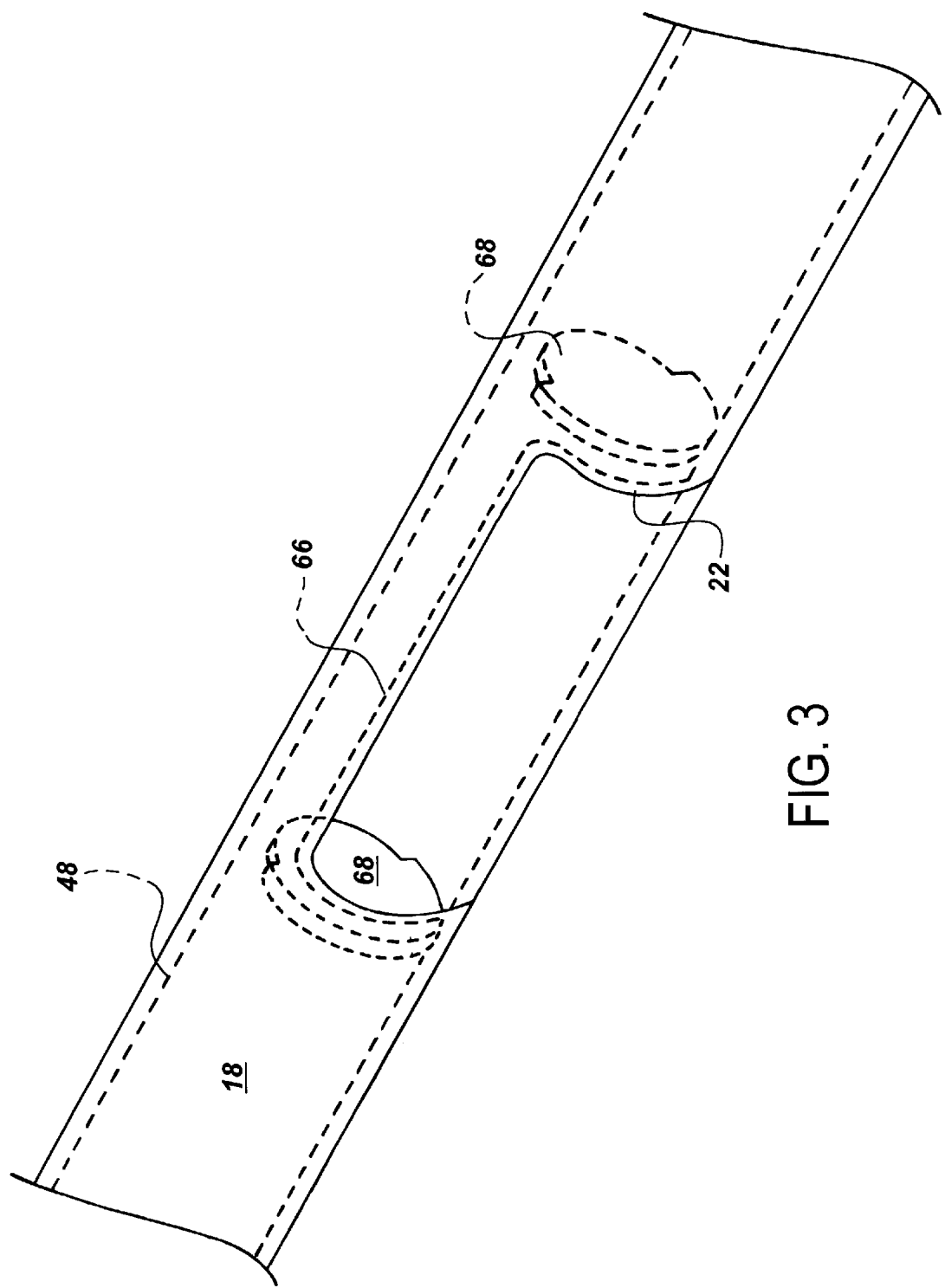
FIG. 3 is a top plan view, partially broken away, of an outer tubular casing and the inner receiving rod of the bulk sampling tool according to the present invention, wherein the inner receiving rod components are shown mainly in hidden line.

As seen in FIG. 2, the partitions 68 are substantially spherical in shape and have an upper 98, generally half moon-shaped, portion with a diameter $d_1$ and a lower 90, generally half moon-shaped, portion with a diameter $d_2$, wherein diameter $d_1$ is greater than diameter $d_2$. Moreover, diameter $d_1$ is approximately at least equal to diameter $d_3$ of the outer wall 69 of the inner rod 48, and diameter $d_2$ is approximately at least equal to the diameter $d_4$ of the inner wall 60 of the inner rod 48, wherein diameter $d_3$ is greater than diameter $d_4$. When removable partitions 68 having these overall dimensions are located in the partition receiving slots 62, non-communicating bulk sample ports 66 are formed in the inner receiving rod 48, thereby preventing sample leakage or contamination between adjacent ports 66, and permitting easy disassembly and cleaning of the inner rod 48.

In an alternative embodiment, the bulk sample ports 66 can act as die receiving means for containing dies (not shown) of various sizes, shapes and number; such as the dies disclosed in U.S. Pat. No. 5,337,620 and U.S. Pat. No. 5,440,941. The apertures 22 in the outer tubular casing 18 are dimensioned such that each is smaller than the bulk sample ports 66 on the inner receiving rod 48, in order to retain the dies securely inside the inner receiving rod 48, even when the sample ports are in an opened position.

The embodiment in FIGS. 4–6 depicts the grooved guide pin receiving pattern 30 as comprising a first notch setting position A, an intermediate position B, and a second notch setting position C for receiving said pin 86. The first notch setting position A enables the sample port 66 of the receiving rod 48 to correspondingly align with the apertures 22 of the outer casing 18 such that a bulk sample be collected. The second notch setting position C enables the sample port of the receiving rod into a correspondingly offset alignment with the apertures of the outer casing 18 in order to completely retain a bulk sample within the confines of a closed bulk sample and thereby prevent the sample contained within the sample port 66 from being released. It should be noted that the grooved guide pin receiving pattern 30 embodiment shown in FIGS. 4–6 is a preferred embodiment, and that additional grooved guide pin receiving patterns can also be used.

The pattern groove 30 and guide pin 86 also functions as a travelstop in that the once the guide pin rests in either open notch position A or in closed notch position C, at that point the inner receiving rod 48 is held in a predetermined relationship such that the sample ports 66 and the apertures 22 on the outer casing 18 can be aligned or offset, as best seen in FIGS. 4–6.

When the device 100 is inserted into a material for sampling, the inner rod 48 is rotated at the handle 88 such that the apertures 22 align relative to the sample ports 66, allowing the sample material to be collected. In order to withdraw the device 100 from the sampling material and maintain the sample within each filled bulk sample port 66, the inner rod 48 is rotated such that the apertures 22 in the outer casing 18 no longer align with the sampling ports 66. The samples are removed from the bulk sample ports 66 for testing and the like by manipulating the inner receiving rod 48 and sample ports 66 relative to the apertures 22, in order to allow the sample ports 22 to discharge the sampled material contained therein by opening the bulk sample ports 66. The removable partitions 68 located between each sample port 66 within partition receiving slots 62 remain trapped between the outer casing 18 and the inner receiving rod 48.

FIGS. 4–6 illustrate a range of positions that the sampling device 100 can be in manipulated in order to collect a bulk sample, wherein manipulation of the handle 88 located on the receiving rod 48 enables movement and rotation of the receiving rod 48, thereby guiding the guide pin 86 along the grooved guide pin receiving pattern 30 of the outer casing 18. As depicted in FIG. 4 the bulk sample port 66 of device 100 is in a completely open position such that a bulk sample (not shown) can be received within the sample port. In FIG. 4, the bulk sample port 66 is in the open position when pin 86 is in the first or open notch setting position A of groove pattern 30. When the handle 88 is turned and the pin 86 is moved to intermediate notch position B, as depicted in FIG. 5, the bulk sample port 66 is partly closed by misaligning inner rod 48 with aperture 22. When pin 86 is moved to the second or closed notch position C by turning handle 88, as depicted in FIG. 6, the bulk sample port 66 is offset from the aperture 22 in outer casing 18 and in a completely closed position. The sampling device 100 may be taken out of the sampling mixture at this time.

It should be emphasized that the bulk sampling device 100 can be of a variety of lengths such as three, four, or more feet. All that would be required is to have an outer tubular shaped casing 18 and inner receiving rod 48 with a corresponding length. It should also be noted that although a handle 88 is shown as a manipulating member, any number of appropriate shapes such as a ring (not shown) or other curved shape could be used in its place to facilitate the manipulation of the bulk sampling device 100 into positions ranging from opened to closed as discussed above. The receiving rod 48 may have a permanently attached handle or the handle 88 may be threadingly attached (not shown) for easy removal from the receiving rod, thereby making the device more modular and facilitating easy cleaning of the receiving rod 48.

The outer tubular casing 18, the inner receiving rod 48, the cone 28, the handle 88 and the removable partitions 68 are preferably made of stainless steel. However, all or some combination of these components can be made from a synthetic material such as a fluorinated polymer resin commercially available as TEFLON, or an acetal polymer resin, commercially available as DELRIN. In a more preferred embodiment, the bulk sampling device 100 is approximately three (3) feet long from the top of handle to the tip of the cone; made entirely of 316 SS; has an outer casing 18 with a diameter of 1.5 inches; and has a row of three, 1.125 inch by 4.0 inch non-communicating sample ports, wherein each sample port can hold about 90 cc of a given sample.

The design of the bulk sampling device permits easy cleaning of the entire device because it is largely and easily dismantled and modular to facilitate a thorough and efficient cleaning process. The removable partitions are easily removed from the inner receiving rod such that upon removal of the cone tip and the partitions, and even the handle each portion of the device can be adequately cleaned.

It is to be understood that the present invention is not limited to the sole embodiment described above, but encompasses any and all embodiments within the scope of the following claims.

I claim:

1. A bulk sampling device for taking multiple volumetric samples from the same area and at different depths of powder or semi-solid mixtures, comprising:

a hollow outer tubular casing;

an inner bulk sampling receiving rod;

said hollow outer casing having a predetermined length, an interior wall dimensioned to smoothly receive said inner receiving rod, at least one aperture, a distal end and an opened proximate end for receiving said inner receiving rod;

the proximate end of said hollow outer casing having a grooved guide pin receiving pattern;

the distal end of said hollow outer casing having first engaging means;

said inner receiving rod having a predetermined length for fitting snugly and removably inside said outer tubular casing, a proximate end, a distal end, an inner wall, an outer wall, at least one bulk sample receiving port, at least one removable partition and at least one partition receiving slot;

the proximate end of said inner receiving rod has a handle and a guide pin;

wherein the bulk sample port being aligned with and having greater dimensions than the aperture in said tubular casing such that the partition receiving slot is positioned adjacent the bulk sample port and the removable partition is positioned within the receiving slot such that each of the bulk sample ports are non-communicating with each other and the partition remains trapped within the receiving slot when said inner receiving rod is completely inserted into said hollow outer casing; and a solid cone having a proximate end, a distal end, and second engaging means located at said proximate end which engages said first engaging means and closes the distal end of said outer tubular casing;

wherein manipulation of the handle of said receiving rod enables movement and rotation of said receiving rod thereby guiding the guide pin along the grooved guide pin receiving pattern of said outer hollow tubular casing such that when the bulk sample port is offset from the aperture in said outer tubular casing the bulk sample port is in a closed position.

2. The device according to claim 1, wherein:

the grooved guide pin receiving pattern comprises a first notch setting position and second notch setting position for receiving said pin;

whereby the first setting position enables the sample port of said receiving rod to correspondingly align with the apertures of said outer casing such the sample port is opened and sampling can occur and the second setting position enables the sample port of said receiving rod to offset alignment with the apertures of said outer casing such that the sample port is closed.

3. The device according to claim 1, wherein:

there are a plurality of removable partitions and a plurality of receiving slots; and the partitions each comprise an upper substantially half moon-shaped portion with a diameter $d_1$ and a lower substantially half moon-shaped portion with a diameter $d_2$, wherein diameter $d_1$ is greater than diameter $d_2$.

4. The device according to claim 3, wherein:

the inner wall of said inner receiving rod has a diameter $d_4$ being approximately equal to the diameter $d_2$; and the outer wall of the inner receiving rod has a diameter $d_3$ being approximately equal to the diameter $d_1$;

wherein diameter $d_3$ is greater than diameter $d_4$.

5. The device according to claim 1, wherein:

said device is constructed entirely from stainless steel.

6. The device according to claim 1, wherein:

the handle is removable.

7. A process of obtaining bulk samples from a blended pharmaceutical, food, or cosmetic mixture by the use of the bulk sampling device according to claim 1 comprising the steps of:

a) positioning into a blended pharmaceutical, food, or cosmetic mixture the sampling device in a closed position;

b) turning the handle of the receiving rod and rotating the receiving rod to align the non-communicating sample ports with the apertures thereby opening and exposing the sample ports for receiving said pharmaceutical, food, or cosmetic mixture and retaining the partitions within the receiving rod;

c) taking a bulk sample volumes of said pharmaceutical, food, or cosmetic mixture;

d) turning the handle of the receiving rod to rotate the receiving rod to close off apertures in the outer tubular casing thereby closing the sample ports; and e) removing the bulk sampling device from the pharmaceutical, food, or cosmetic mixture.

8. The process according to claim 7, further comprising the steps of:

f) placing collection means beneath sample ports; and g) turning the handle of the receiving rod and rotating the receiving rod to align the non-communicating sample ports with the apertures thereby opening the sample ports and discharging the sample mixture from the sample ports while retaining the partitions within the receiving rod.

9. The process according to claim 8, further comprising the steps of:

h) cleaning the bulk sample device by pulling the receiving rod out of the outer tubular casing;

i) dismantling the inner receiving rod by removing the partitions and the handle and thoroughly cleaning; and j) dismantling the outer tubular casing by removing the cone and thoroughly cleaning.

* * * * *